United States Patent [19]

Scripps

[11] Patent Number: 4,846,815
[45] Date of Patent: Jul. 11, 1989

[54] DISPOSABLE DIAPER HAVING AN IMPROVED FASTENING DEVICE

[75] Inventor: Charles L. Scripps, Brookfield, Wis.

[73] Assignee: The Procter & Gamble Company, Cincinnati, Ohio

[21] Appl. No.: 132,281

[22] Filed: Dec. 18, 1987

Related U.S. Application Data

[63] Continuation-in-part of Ser. No. 7,841, Jan. 26, 1987, abandoned.

[51] Int. Cl.$^4$ .............................................. A61F 13/16
[52] U.S. Cl. ........................... 604/391; 128/DIG. 15; 24/442
[58] Field of Search ................ 128/DIG. 15, 524, 577, 128/284; 52/DIG. 13; 2/DIG. 6; 24/442, 448; 428/100, 120; 604/378, 391

[56] References Cited

U.S. PATENT DOCUMENTS

| | | |
|---|---|---|
| 3,081,772 | 3/1963 | Brooks et al. . |
| 3,110,312 | 11/1963 | Wirth . |
| 3,138,841 | 6/1964 | Naimer . |
| 3,141,461 | 7/1964 | Farris ................................ 604/391 |
| 3,147,528 | 9/1964 | Erb . |
| 3,150,664 | 9/1964 | Noel . |
| 3,196,511 | 7/1965 | Kintner . |
| 3,266,113 | 8/1966 | Flanagan, Jr. . |
| 3,359,980 | 12/1967 | Rosenblatt . |
| 3,550,837 | 12/1970 | Erb . |
| 3,577,607 | 5/1971 | Ikoma . |
| 3,618,608 | 11/1971 | Brink . |
| 3,653,381 | 4/1972 | Warnken . |
| 3,708,833 | 1/1973 | Ribich et al. . |
| 3,715,415 | 2/1973 | Erb . |
| 3,848,594 | 11/1974 | Buell . |
| 3,882,871 | 5/1975 | Taniguchi ........................... 128/284 |
| 3,900,652 | 8/1975 | Uraya et al. . |
| 3,905,071 | 9/1975 | Brumlik . |
| 3,943,981 | 3/1976 | De Brabander . |
| 3,955,575 | 5/1976 | Okuda . |
| 4,051,854 | 10/1977 | Aaron . |
| 4,110,138 | 8/1978 | Nomura et al. . |
| 4,114,621 | 9/1978 | Mims, Jr. . |
| 4,158,906 | 6/1979 | Watson . |
| 4,169,303 | 10/1979 | Lemelson . |
| 4,216,257 | 8/1980 | Schams et al. . |
| 4,241,462 | 12/1980 | Tagawa et al. . |

(List continued on next page.)

FOREIGN PATENT DOCUMENTS

| | | |
|---|---|---|
| 0233364 | 8/1987 | European Pat. Off. . |
| 0235014A2 | 9/1987 | European Pat. Off. . |
| 754302 | 1/1971 | France ................................ 24/442 |
| 59-88903 | 5/1984 | Japan . |
| 1238202 | 10/1986 | Japan ................................. 24/442 |
| 1235503 | 6/1971 | United Kingdom . |
| 1299897 | 12/1972 | United Kingdom . |
| 1343604 | 1/1974 | United Kingdom . |

Primary Examiner—Randall L. Green
Attorney, Agent, or Firm—Steven W. Miller; John M. Pollaro; Fredrick H. Braun

[57] ABSTRACT

A disposable diaper comprising an absorbent core that is encased between a liquid pervious topsheet and a liquid impervious backsheet, elasticized leg openings, and a fastening device for securing the diaper on a wearer. The fastening device comprises a first member having a plurality of fiber elements and a second member having a plurality of engaging elements that are mechanically engageable with the fiber elements of the first member. The engaging elements are disposed and manufactured so as to provide a fastening device that is capable of resisting the peel forces and shear stress that are encountered during use and that is comfortable and skin friendly for the wearer. Each of the engaging elements thus preferably comprises a stem and an enlarged head positioned on one end of the stem; the head having a smooth, generally convex top surface that provides a skin friendly second member and a bottom surface that extends radially outwardly from the stem to engage the fiber elements of the first member. The fiber elements of the first member and the engaging elements of the second member are configured to maximize peel resistance such that the fastening device has a fiber overhang ratio of at least about 2:1 and a height ratio of at least about 5:1.

20 Claims, 3 Drawing Sheets

U.S. PATENT DOCUMENTS

| | | |
|---|---|---|
| 4,259,957 | 4/1981 | Sonnenstein et al. |
| 4,290,174 | 9/1981 | Kalleberg . |
| 4,290,832 | 9/1981 | Kalleberg ............................... 156/72 |
| 4,307,493 | 12/1981 | Ochiai . |
| 4,322,875 | 4/1982 | Brown et al. |
| 4,330,907 | 5/1982 | Ochiai . |
| 4,402,690 | 9/1983 | Redfern ............................... 128/284 |
| 4,410,327 | 10/1983 | Baggaley . |
| 4,454,183 | 7/1984 | Wollman . |
| 4,475,912 | 10/1984 | Coates . |
| 4,509,512 | 4/1985 | LeClercq . |
| 4,537,591 | 8/1985 | Coates . |
| 4,541,154 | 9/1985 | Ito et al. |
| 4,560,381 | 12/1985 | Southwell . |
| 4,563,380 | 1/1986 | Black et al. |
| 4,568,342 | 2/1986 | Davis . |
| 4,576,599 | 3/1986 | Lipner . |
| 4,576,601 | 3/1986 | Brain . |
| 4,577,591 | 3/1986 | Wesseldine . |
| 4,581,772 | 4/1986 | Smith . |
| 4,610,680 | 9/1986 | LaFleur . |
| 4,617,022 | 10/1986 | Pignuel et al. |
| 4,671,793 | 6/1987 | Hults et al. |
| 4,680,030 | 7/1987 | Coates . |
| 4,681,581 | 7/1987 | Coates ............................... 604/391 |
| 4,699,622 | 10/1987 | Toussant et al. |
| 4,728,326 | 3/1988 | Gilles . |

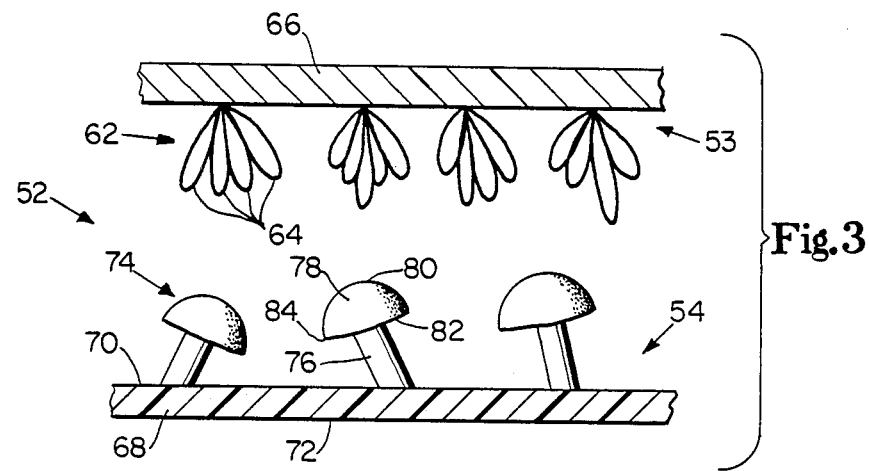
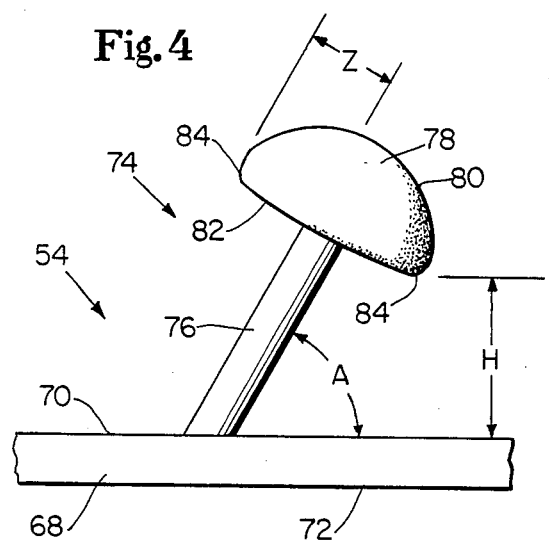

DISPOSABLE DIAPER HAVING AN IMPROVED FASTENING DEVICE

This is a continuation-in-part of application Ser. No. 007,841, filed on Jan. 26, 1987, now abandoned.

FIELD OF THE INVENTION

This invention relates to disposable diapers having fastening devices, and more particularly, to a mechanical fastening device for such disposable diapers that is both skin friendly and capable of resisting the peel forces and shear stress encountered during use.

BACKGROUND OF THE INVENTION

Disposable diapers are well known articles of manufacture that are worn by infants and incontinent persons. Disposable diapers are worn about the lower torso and are intended to absorb and contain urine and feces, thereby preventing such body exudates from soiling, wetting, or otherwise contaminating articles (e.g., clothing, bedding, etc.) that come in contact with the diaper wearer.

In general, disposable diapers have the same basic structure comprising an absorbent core encased between a liquid pervious, user-contacting topsheet and a liquid impervious backsheet. The prior art, of course, teaches numerous variations of and elements in addition to the basic topsheet, backsheet, and absorbent core arrangement. For example, an improvement in performance of disposable diapers has been achieved by the addition of elastic means along portions of the diaper contacting the wearer's thighs or waist, thereby providing elasticized leg or waist openings when the diaper is worn.

When using a disposable diaper having elasticized leg openings, the diaper user fits the diaper on the wearer and fastens it about the wearer's waist by a fastening device to thereby affect a side closure. Fitting the diaper about the wearer usually requires the front and back waist portions of the diaper to overlap each other. Disposable diapers are provided with a fastening device having a first member and a second member which engage each other to provide such a side closure in the front and back waist portions. Since proper and sustained fit about the waist and legs of the wearer is vital for optimal performance in terms of minimizing leakage of exudates out of the diaper, a fastening device must be able to provide an effective side closure in which the front and back waist portions are maintained in an overlapping configuration. Thus, the first and second members must be designed to securely engage each other so that they do not separate due to peel forces and shear stress that are encountered by the fastening device during use.

Another important design criteria in providing a fastening device on a disposable diaper is that the fastening device be comfortable for the wearer. In use, the fastening device may come in contact with the bare skin of the wearer. For example, if one of the members of the fastening device is disposed on the outside of the diaper it may not be completely covered during use such that it will come in contact with the wearer, or since the waist portions are generally highly flexible areas which can fold under during wear, a portion of the fastening device can be exposed to the skin of the wearer. Thus, if the fastening device is "skin friendly" (i.e., it does not contain sharp, rough or jagged edges, elements or prongs) the fastening device should not abrade or irritate the skin of the wearer.

A number of concepts have been proposed for adhesively fastening a disposable diaper about the waist of the wearer. For example, U.S. Pat. No. 3,848,594 issued to K. B. Buell on Nov. 19, 1974, teaches an adhesive tape fastening system for effecting a side closure having an improved manufacturer's joint, referred to as Y-bond. Adhesive tape fasteners have, however, a number of shortcomings, one of which is that they are easily contaminated by oils and powders that come in contact with the adhesive on the fastening tapes such that the adhesive does not adhere to the diaper with suffient strength to provide an effective side closure. In addition, an adhesive tape fastener may rip the backsheet of the diaper during the process of unfastening it to check if the diaper has been soiled or to adjust its fit, thereby leaving a hole in the backsheet of the diaper and rendering the fastener unrefastenable and the diaper unuseable. Thus, it would advantageous to provide a fastening device that is not easily contaminated by oils and powders, that is more convenient to refasten, and that does not render the diaper or the fastening device unuseable after unfastening.

Since adhesive tape fasteners are not practical for use on reuseable diapers, a number of concepts have been proposed for providing a reuseable diaper with a mechanical fastener having hooks and loops disposed on the body of the diaper. For example, U.S. Pat. No. 3,359,980 which issued to C. L. Rosenblatt on Dec. 26, 1967; U.S. Pat. No. 4,402,690 which issued to R. Redfern on Sept. 6, 1983; and U.S. Pat. No. 3,618,608 which issued to M. E. Brink on Nov. 9, 1971 all teach reuseable diapers having hook and loop type fasteners.

While hook and loop type fasteners generally provide a fastening device that is not easily contaminated by oils and powders and is more convenient for refastening than adhesive fastening tapes, hook and loop type fasteners are generally not comfortable nor skin friendly. The "hook" members may have sharp, jagged edges or jagged members that can puncture, abrade or irritate the skin of the wearer. This is especially true of hook and loop type fasteners wherein the hook elements are formed by cutting a filament loop. Jagged edges are formed on both the hook and on the resulting non-functional prong that is formed in the cutting process. Thus, it would be advantageous to provide a mechanical fastener that is capable of resisting the peel forces and shear stress that are encountered during use and that is comfortable for the wearer because it is skin friendly so that it minimizes discomfort and skin irritation of the wearer.

It is, therefore, an object of the present invention to provide a disposable diaper having an improved fastening device.

It is a further object of the present invention to provide a disposable diaper having a fastening device that maintains the fit of the diaper at the waist and at the elasticized leg openings during wearing.

It is an additional object of the present invention to provide a disposable diaper having a fastening device that is not easily contaminated by oil and powders and that is refastenable.

It is another object of the present invention to provide a disposable diaper having a fastening device that provides wearer comfort and ease of handling for the user.

It is a still further object of the present invention to provide a disposable diaper having a mechanical fastening device that is skin friendly and able to resist the peel forces and shear stress encountered during use.

These and other objects of the present invention will be more readily apparent when considered in reference to the following description and when taken into connection with the accompanying drawings.

SUMMARY OF THE INVENTION

According to the present invention, a disposable diaper having elasticized leg openings is manufactured such that an absorbent core is encased between a liquid pervious topsheet and a liquid impervious backsheet.

When the elasticized disposable diaper is placed around the waist of the wearer, the waist portions of the diaper are made to overlap. The disposable diaper of the present invention is provided with a fastening device which affixes the overlapping portions of the waist portions to each other and maintains them in contact with each other during use. The fastening device prevents separation of the overlapping waist portions because the fastening device is able to resist the peel forces and shear stress encountered when the diaper is worn.

While the fastening device may take many forms, the fastening device preferably comprises a first member comprising a plurality of fiber elements and a second member engagable with the fiber elements of the first member. The first member thus provides an area on one of the waist portions, that when brought into contact with the other overlapping waist portion, becomes mechanically entangled with the second member. The second member preferably comprises a flexible base and a plurality of engaging elements extending from the first surface of the base. The engaging elements should be disposed on the base and manufactured so as to provide the necessary resistance to peel forces and shear stress encountered during use. In order to provide the resistance to such forces and to maintain comfort for the wearer and skin friendliness, each of the engaging elements is flexible and resilient and comprises a stem supported at one end on the base, and an enlarged head positioned at the end of the stem opposite of the base. The head has a smooth, generally convex top surface that provides no jagged edges so that the second member is skin friendly. The bottom surface of the head extends radially outwardly from the stem to the periphery of the top surface so as to engage the fiber elements of the first member and provide the necessary resistance to peel forces and shear stress.

In order to provide the necessary resistance to peel forces and to engage the maximum number of fiber elements of the first member, the fastening device has a fiber overhang ratio of at least about 2:1 and a height ratio of at least about 5:1.

BRIEF DESCRIPTION OF THE DRAWING

FIG. 3 is an enlarged fragmentary sectional view showing the first and second members of the present invention.

FIG. 4 is an enlarged sectional view of an engaging element of the present invention.

DETAILED DESCRIPTION OF THE INVENTION

Figure 1:
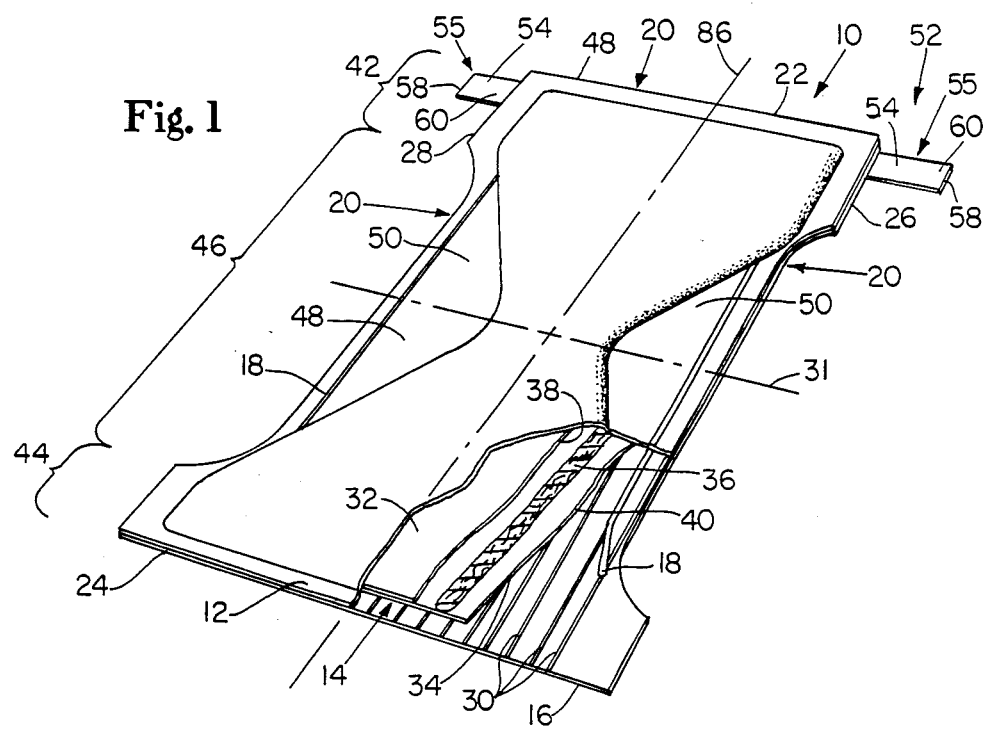
FIG. 1 is a partially cut-away perspective view of an elasticized disposable diaper incorporating the improved fastening device of the present invention.

Referring to the drawings, there is shown a preferred embodiment of the present invention as it would be used in a disposable diaper intended to be worn by an infant. As used herein, the term "disposable diaper" refers to a garment generally worn by infants or incontinent persons, which is drawn up between the legs and fastened about the waist of the wearer and further, which is intended to be discarded after a single use (i.e., it is not intended to be laundered or otherwise restored and reused).

FIG. 1 is a partially cut-away perspective view of the disposable diaper 10 of the present invention prior to its being folded and placed on the diaper wearer by the diaper user. As can be seen in FIG. 1, a preferred diaper 10 comprises a liquid pervious topsheet 12, an absorbent core 14, a liquid impervious backsheet 16 and elastic members 18. While the topsheet 12, the absorbent core 14, the backsheet 16, and the elastic members 18 may be assembled in a variety of well known configurations, a preferred disposable diaper configuration is described generally in U.S. Pat. No. 3,860,003 entitled "Contractable Side Portions for Disposable Diaper", which issued to K. B. Buell on Jan. 14, 1975, and which patent is incorporated herein by reference.

Figure 2:
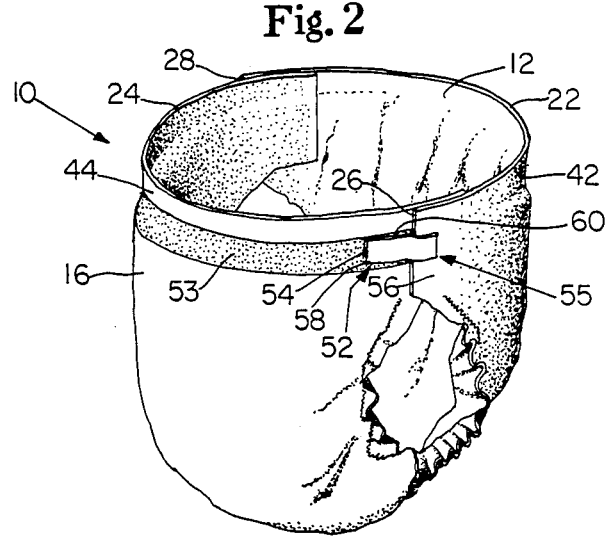
FIG. 2 is a partially cut-away perspective view showing the disposable diaper of FIG. 1 in the configuration it would assume when placed on a wearer.

FIGS. 1 and 2 show a preferred embodiment of the diaper 10 in which the topsheet 12 and the backsheet 16 are coextensive and have length and width dimensions generally larger than those of the absorbent core 14. The topsheet 12 is superposed on the backsheet 16 thereby forming the periphery 20 of diaper 10. The periphery 20 defines the outer perimeter or, in other words, the outer extent of the diaper 10. The periphery 20 comprises a first end 22, a second end 24, a first longitudinal side 26, and a second longitudinal side 28.

The topsheet 12 may be affixed to the backsheet 16 in any suitable manner as is well known in the diaper manufacturing art. In a preferred embodiment, a multiplicity of longitudinal adhesive bands 30 of preferably hot-melt adhesive are applied along the full length of the backsheet 16 generally parallel to the longitudinal centerline 86 of the backsheet 16. The longitudinal adhesive bands 30 serve to affix the topsheet 12 to the backsheet 16 at those points where these three components come together. The extent and location of the points where the topsheet 12, backsheet 16, and longitudinal adhesive bands 30 come together will depend on the spacing between the longitudinal adhesive bands 30 and on the distance the topsheet 12 and the backsheet 16 extend beyond the absorbent core 14. The number of longitudinal adhesive bands 30 and the spacing therebetween should be sufficient to securely bond the topsheet 12 to the backsheet 16 in the area between the periphery 20 and the edge of the absorbent means 14.

A hot-melt adhesive suitable for use as longitudinal adhesive bands 30 is manufactured by Eastman Chemical Products Company of Kingsport, Tenn. and marketed under the tradename Eastobond A-3. It will be noted that the above described manner of affixing the topsheet 12 to the backsheet 16 causes the topsheet 12 to be affixed to the backsheet 16 intermittently along the first and second ends, 22 and 24. The absorbent core 14 is thereby encased between the topsheet 12 and the backsheet 16. Of course, many alternative methods of affixing the topsheet 12 to the backsheet 16 may be used with satisfactory results. For example, the topsheet 12 may be affixed to the backsheet 16 indirectly rather than directly as shown in FIG. 1. Thus, an intermediate member may be used to affix the topsheet 12 to the backsheet 16.

The diaper 10 has first and second waist portions 42 and 44 extending, respectively, from the first end 22 and the second end 24 of the diaper periphery 20 toward the lateral centerline 31 of the diaper 10 a distance from about 1/5 to about ⅓ the length of the diaper. The waist portions 42 and 44 comprise those portions of the diaper 10 which, when worn, encircle the waist of the wearer. The crotch portion 46 is that portion of the diaper 10 between the first and second waist portions 42 and 44, and comprises that portion of the diaper 10 which, when worn, is positioned between the legs of the wearer and covers the lower torso of the wearer.

The absorbent core 14 may be any means which is generally compressible, conformable, non-irritating to the wearer's skin, and which is capable of absorbing and retaining liquids and certain body exudates. A preferred absorbent core 14 has first and second opposed faces 32 and 34, respectively, and comprises an absorbent layer 36 and first and second tissue layers 38 and 40, respectively. The first and second tissue layers 38 and 40 overlay the major surfaces of the absorbent layer 36 to form the first and second opposed faces 32 and 34 of the absorbent core 14.

The absorbent layer 36 is intended to absorb and contain liquid and may be manufactured in a wide variety of sizes and shapes (e.g., rectangular, hourglass, etc.) and from a wide variety of liquid absorbent materials commonly used in disposable diapers, such as comminuted wood pulp which is generally referred to as airfelt. Other liquid absorbing materials may also be used in the manufacture of the preferred embodiment shown in FIGS. 1 and 2 weighs from about 30 to about 56 grams and has a generally uniform caliper. It should be understood, however, that the size, shape, configuration, and total absorbent capacity of the absorbent layer 36 may be varied to accommodate wearers ranging from infants through adults. Therefore, the dimensions, shape and configuration of the absorbent layer 36 may be varied (e.g. the absorbent layer 36 may have a varying caliper, or a hydrophilic gradient, or may contain absorbent gelling materials).

The first and second tissue layers, 38 and 40, are intended to improve the tensile strength of the absorbent core 14 and to reduce the tendency of the absorbent layer 36 to split, lump or ball when wetted. The first and second tissue layers, 38 and 40, also help to improve lateral wicking of liquids, thereby providing a more even distribution of liquid in the absorbent layer 36. While a number of materials and manufacturing techniques may be used to manufacture the first and second tissue layers, 38 and 40, satisfactory results have been obtained with sheets of tissue paper having a basis weight of approximately 16 gms per square meter (10 pounds per 3000 square feet) and having an air permeability of approximately 30 cubic meters per minute per square meter (100 cubic feet per minute per square foot) at a pressure differential of 13 mm (0.5 inch) of water. While the first and second tissue layers 38 and 40, are preferably coterminous with the absorbent layer 36, they may have different dimensions, a different configuration, or they may be omitted entirely.

The absorbent core 14 is superimposed on the backsheet 16 and is preferably affixed thereto by any means as is well known in the diaper art. For example, the absorbent core 14 may be secured to the backsheet 16 by a uniform continuous layer of adhesive, a patterned layer of adhesive, or an array of lines or spots of adhesive. In the preferred embodiment illustrated in FIGS. 1 and 2, the longitudinal adhesive bands 30 are used to affix the absorbent core 14 to the backsheet 16.

The backsheet 16 is impervious to liquids and prevents liquids absorbed and contained by the absorbent core 14 from wetting the undergarments, clothing, bedding, and other objects which contact the wearer of the disposable diaper 10. Preferably the backsheet 16 is a polyethylene film of from about 0.0005 to about 0.002 inches (about 0.012 to about 0.051 mm) thick, although other liquid impermeable materials may also be used. A suitable polyethylene film is manufactured by Monsanto Chemical Company and marketed in the trade as Film No. 8020. The backsheet 16 is preferably embossed and/or matte finished to provide a more clothlike appearance. Further, the backsheet 16 may have passages which permit vapors to escape from the absorbent core 14 while still preventing liquid from passing through the backsheet 16.

In a preferred embodiment, the backsheet 16 has a modified hourglass shape extending beyond the absorbent layer 36 a minimum distance of at least about 0.5 inches (about 1.3 cm) around the entire diaper periphery 20. The marginal portion 48 is that portion of the diaper 10 between the diaper periphery 20 and the edge of the absorbent layer 36 and comprises longitudinal marginal portions 50 adjacent the first and second longitudinal sides 26 and 28, respectively in the crotch portion 46.

The topsheet 12 is compliant, soft feeling, and non-irritating to the wearer's skin and prevents the wearer of the diaper 10 from contacting the absorbent core 14. Further, the topsheet 12 is liquid pervious permitting liquids to readily penetrate through its thickness. A suitable topsheet 12 may be manufactured from a wide range of materials, such as natural fibers (e.g., wood or cotton fibers), synthetic fibers (e.g., polyester, polyethylene, polypropylene), or a combination thereof. Alternatively, the topsheet 12 may be a foam, such as the reticulated foams which are well known in the art or of any of the formed films which are also well known in the art.

There are a number of manufacturing techniques which may be used to manufacture the topsheet 12. For example, the topsheet 12 may be woven, nonwoven, spunbonded, carded, or the like. A preferred topsheet 12 is carded, and the thermally bonded by means well known to those skilled in the nonwoven fabrics art. Preferably, the topsheet 12 has a weight of from about 18 to about 25 grams per square meter, a minimum dry tensile strength of at least about 400 grams per centimeter in the machine direction and a wet tensile of at least about 55 grams per centimeter in the cross machine direction.

The elastic members 18 are affixed to the diaper 10 along both longitudinal marginal portions 50 so that they tend to draw and hold the diaper 10 against the legs of the wearer. Thus, when worn the diaper 10 will have elasticized leg openings. While this result may be accomplished by any of several means as are well known in the diaper art, a particularly preferred diaper construction incorporating elastic is described in detail in the hereinbefore referenced U.S. Pat. No. 3,860,003. In addition, a method and apparatus suitable for manufacturing a disposable diaper having elastic leg bands are described in U.S. Pat. No. 4,081,301 entitled "Method and Apparatus for Continuously Attaching Discrete, Stretched Elastic Strands of Predetermined Isolated Portions of Disposable Absorbent Products" which issued to K. B. Buell on Mar. 28, 1978 and which patent is incorporated herein by reference.

Relating the teachings of U.S. Pat. No. 3,860,003 to the preferred embodiment shown in FIGS. 1 and 2, it can be seen that the elastic members 18 are operatively associated with both longitudinal marginal portions 50 in the crotch portion 46 in an elastically contractible condition so that in a normally unrestrained configuration the elastic members 18 effectively contract or gather the longitudinal marginal portions 50.

As used herein the term "operatively associated with" refers to two or more components which act together. In the preferred embodiment shown in FIGS. 1 and 2, the elastic members 18 are operatively associated with both longitudinal marginal portions 50 in the crotch portion 46. Thus, the elastic members 18 are affixed to the longitudinal marginal portions 50 so as to cause the longitudinal marginal portions 50 in the crotch portion 46 to be contracted or gathered. A suitable method for incorporating elastic members 18 into a disposable diaper is described in the aforesaid U.S. Pat. No. 4,081,301.

In the preferred embodiment illustrated, the elastic members 18 are affixed to a portion of the backsheet 16 in the longitudinal marginal portions 50. A suitable adhesive will be flexible and of sufficient adhesiveness to hold the elastic member 18 to the backsheet 16 while the elastic member 18 is stretched. An adhesive which has been used with satisfactory results is manufactured by Findley Adhesives Corporation of Elm Grove, Wis. and is marketed under the tradename Findley 581-334-01, although the elastic members 18 may be affixed to the diaper 10 in any of several other ways which are known in the art. For example, the elastic members 18 may be ultrasonically bonded or heat/pressure sealed into the diaper using a variety of bonding patterns or the elastic members 18 may simply be glued to the diaper 10.

The elastic members 18 can be operatively associated with the longitudinal marginal portions 50 in an elastically contractible condition in at least two ways. For example, the elastic member 18 may be stretched and while the stretched condition affixed to the uncontracted and unstretched longitudinal marginal portions 50. Alternatively, the longitudinal marginal portions 50 may be contracted (e.g., by pleating) and then affixing the unstretched elastic member 18 to the contracted longitudinal marginal portions 50.

Suitable elastic members 18 may be manufactured from a wide variety of elastic materials such as natural rubber, or elastomeric films such as Kraton, ethylene propylene-dimonomer, polyurethane, elastomeric foams, formed elastic scrim, or heat shrinkable material.

In addition, the elastic member 18 may take a multitude of configurations. For example, the width of the elastic members 18 may be varied from about 0.38 mm–25 mm (0.015 inches to 1.0 inches) or more; the elastic members 18 may comprise a single strand of elastic material or may comprise several parallel or non-parallel strands of elastic material; or the elastic members 18 may be rectilinear or curvilinear.

One material which has been found to work well as an elastic member 18 is an elastic tape having a cross section of about 0.18 mm by about 6.4 mm (0.007 inches by 0.25 inches) and which is manufactured from natural rubber. Such a product is marketed by Easthampton Rubber Thread Company under the tradename L-1900 rubber compound. The preferred elastic member 18 produces a tensile force of about 100 grams when stretched 100 percent from its relaxed condition.

The diaper 10 is provided with a fastening device 52 for maintaining the first and second waist portions 42 and 44 in an overlapping configuration when the diaper 10 is worn. Thus, the diaper 10 is fitted to the wearer and a side closure is formed. The fastening device 52, therefore, should not only resist the shear stress but also the peel forces which act on the waist portions during use.

While the fastening device 52 may take many alternative configurations, a fastening device 52 suitable for use on a disposable diaper 10 must be capable of resisting peel forces and shear stress during use. As used herein the term "shear stress" refers to the distributed forces acting tangentially to the surface of contact of the first and second members 53 and 54 of the fastening device 52 that are encountered during the wearing of the diaper 10. The shear stress tends to cause the first and second members 53 and 54 to shift with respect to each other. Shear stress is to be distinguished from "peel forces" which act on the first and second members 53 and 54 of the fastening device 52 so as to separate and disengage from each other. A disposable diaper will be subjected to peel forces in at least three ways. Peel forces are generated by the movements of the wearer during use as they tend to cause the first and second members to pull away from each other, by the wearer in trying to unfasten the fastening device during wear (this being a special problem for disposable diapers worn by infants because the infant should not be able to unfasten and remove the diaper on its own), and by the user to check the diaper for soiling or to remove the diaper from the wearer. Because the fastening device must be able to be checked and removed by the user and because the user generated peel forces are much higher than the peel forces generated by the first two methods, the fastening device 52 is designed to have a resistance to peel forces (peel resistance) with respect to only the movement and wearer generated methods. It should, therefore, be understood that the peel resistance should only be great enough to prevent failure of the fastening device during the first two methods.

It has been found that the fastening device 52 must be designed so as to resist peel forces of at least about 200 grams, and preferably at least about 500 grams. In addition it has been found that the fastening device 52 should be designed so as to resist shear stress of at least about 500 grams and more preferably at least about 750 grams. Since a mechanical fastening device will typically have a resistance to shear stress much higher than that required for use on a disposable diaper due to the entanglement characteristics of the members, the key strength design criteria for a fastening device 52 for use on a disposable diaper 10 is the peel resistance of the fastening device 52. The peel resistance and the shear stress resistance of the fastening device 52 may readily be determined in accordance with the procedures described hereinafter.

As shown in FIG. 3, the fastening device 52 preferably comprises a first member 53 comprising a plurality of fiber elements 62, preferably loops 64, projecting from a backing 66 and a second member 54 engagable with the fiber elements 62 of the first member 53. As shown, the second member 54 preferably comprises a base 68 having a first surface 70 and a second surface 72, and a plurality of engaging elements 74 extending from the first surface 70 of the base 68. Each of the engaging elements 74 are shown to comprise a stem 76 supported at one end on the base 68 and an enlarged head 78 positioned at the end of the stem 76 opposite of the base 68. The head 78 has a smooth, generally convex top surface 80 adapted to deflect the fiber elements 62 of the first member 53 and to provide a skin friendly surface should the skin of the wearer come in contact with the second member 54, and a bottom surface 82 extending radially outwardly from the stem 76 to the periphery 84 of the top surface 80, the bottom surface 82 being adapted to be engaged by the fiber elements 62.

The first member 53 provides a plurality of fiber elements 62 that engage the bottom surface 82 of the engaging elements 74 to maintain the first and second waist portions 42 and 44 in an overlapping configuration. The first member 53 may be manufactured from a wide range of materials to provide fiber elements 62, preferably the loops 64 as shown in FIG. 3, capable of securely engaging the engaging elements 74 so as to provide the desired peel resistance. Such suitable materials include nylon, polyester, polypropylene or any combination of these materials. A suitable first member 53 comprises a number of fiber loops projecting from a woven backing such as the commercially available material designated "Scotchmate" brand nylon woven loop No. SJ3401 available from Minnesota Mining and Manufacturing Company, St. Paul, Minn. A preferred first member 53 comprises a tricot knit fabric having a plurality of nylon filament loops projecting from a backing of nylon such as the commercially available material designated "Guilford No. 16110" available from Guilford Mills of Greensboro, N.C. Alternatively, the first member 53 may be a non-woven fabric or any other type of fiber material or loop material which are well known in the art.

The first member 53 may be disposed anywhere on the diaper 10 so long as it engages the second member 54 so as to maintain the first and second waist portions 42 and 44 in an overlapping position. For example, the first member 53 may be disposed on the outside surface of the second waist portion 44, on the inside surface of the first waist portion 42, on the fastening surface of a fastening tape, or on any other portion of the diaper 10 which is disposed to engage the second member 54. In addition, the first member 53 may either be integral, a discrete separate element affixed to the diaper 10, or unitary, a single piece of material that is neither divided nor discontinuous with an element of the diaper 10 such as the topsheet 12 or the backsheet 14. While the first member 53 can assume varying sizes and shapes, it preferably comprises one or more integral patches of material positioned across the outside surface of the second waist portion 44 to allow for maximum fit adjustment at the waist of the wearer. The preferred embodiment of the disposable diaper 10 illustrated in FIG. 2 has an elongated, rectangular-shaped, integral first member 53 secured to the outer surface of the second waist portion 44.

The second member 54 is intended to engage the fiber elements 62 of the first member 53 so as to provide a skin friendly, secure side closure for the diaper 10. FIGS. 3 and 4 show a preferred embodiment of the second member 54 of the present invention. The second member 54 comprises a base 68 having a first surface 70, and a second surface 72, and a plurality of engaging elements 74 extending from the first surface 70 of the base 68. Each of the engaging elements 74 has a stem 76 that projects from the first surface 70 of the base 68 and an enlarged head 78 positioned at the end of the stem 76 opposite of the base 68.

The base 68 is intended to provide a strong backing on or into which is imbedded, bonded, woven or fused a plurality of engaging elements 74. While the base 68 may be manufactured from a wide variety of materials commonly used for backings for mechanical fasteners, the base 68 preferably comprises a generally flexible material so as to provide higher peel resistance for the fastening device 52. Suitable backing materials for the base 68 include nylon, polypropylene, polyethylene, or any equivalent material or blend of these materials. The base 68 may also be manufactured using a number of manufacturing techniques as are known in the art. For example, the base 68 may be woven or molded using injection or extrusion techniques. A preferred embodiment of the second member 54 of the present invention has a woven nylon base 68 wherein the second surface 72 is secured to the fastening surface 60 of the fastening tape 55 by any suitable means such as an adhesive.

Figure 6:
FIG. 6 is a perspective view photograph enlarged approximately 35 times of the second member of the present invention.

As shown in FIGS. 3 and 6, a plurality of engaging elements 74 extend from the first surface 70 of the base 68. It has been found that as the density of the engaging elements 74 disposed on the first surface 70 increases so the resistance to peel forces of the fastening device 52 also increases. While a higher density is generally desired, the engaging elements 74 should not, however, be so closely positioned that it will be difficult for the fiber elements 62 to pass around the top surface 80 of the heads 78 to the bottom surface 82. A preferred second member 54 has a density of at least about 100 engaging elements per square inch, and more preferably at least about 180 engaging elements per square inch.

Referring to FIG. 4, a preferred engaging element 74 is shown to comprise a stem 76 and an enlarged head 78 having a top surface 80 and a bottom surface 82. The engaging element 74 is preferably disposed relative to the base at an angle "A" between the stem 76 and the base 68 of between about 30° and about 90° and, more preferably, between about 45° and about 75°. It has been found that when the engaging elements 74 are disposed at such angles, the peel resistance of the fastening device 52 increases. When disposed at such an angle, it is believed that the engaging elements 74 tend to provide a greater peel resistance because more of the fiber elements 62 should be deflected around the top surface 80 to the bottom surface 82 and because the bottom surface 82 is oriented to be adjacent to more fiber elements 62 thereby increasing the potential number of fiber elements 62 engaged. While all of the engaging elements 74 may be disposed at an angle in the same plane, it is preferred that the engaging elements 74 be disposed in random planes as shown in FIGS. 3 and 6 so as to more effectively engage the fiber elements 62 in all directions.

Figure 5:
FIG. 5 is a perspective view photograph enlarged approximately 35 times of a prior art hook-type fastener element used as a fastening device.

A preferred embodiment of the second member 54 is shown in FIG. 6. In particular, FIG. 6 shows the top surface 80 as being particularly skin friendly in comparison to conventional hook-type fasteners. FIG. 5 shows a conventional hook-type fastener element as is well known in the art. As can be seen, the hook member was formed by cutting a filament loop into two elements, the hook member and a non-functional prong. This cutting process leaves a jagged edge on both the end of the hook member as well as the prong. These jagged wearer. As used herein, the term "generally convex" means an arcuate surface projecting outwardly away from the first surface 70 of the base 68 for a major portion of the surface. Thus, heads 78 that have top surfaces 80 that are not completely convex in that they have minor surface variations, indentations, slots or concave surfaces (for example, the shape of the head of a screw) are within the scope of the term generally convex top surfaces 80 of the present invention. A smooth, generally convex top surface 80 also provides a surface more easily capable of deflecting the fiber elements 62 around the periphery 84 of the top surface 80 to the bottom surface 82. In a preferred embodiment of the present invention, the top surface 80 is preferably a semi-spherical or mushroom-like surface as is shown in FIGS. 3, 4, and 6.

Each of the heads 78 also has a bottom surface 82 extending radially outwardly from at least two radii of the stem 76 to provide a surface upon which the fiber elements 62 may be engaged. Thus, the bottom surface 82 is adapted to engage one or more of the fiber elements 62 of the first member 53 and to retain the fiber elements 62 in engagement with the second member 54 until a sufficient peel force is applied by the user to separate the first and second members 53 and 54. While the bottom surface 82 need only be provided along two radii of the stem 76, the bottom surface 82 preferably extends radially outwardly from each radius of the stem 76, around the entire perimeter of the stem 76, to provide an engaging element 74 effective to engage fiber elements 62 in all directions. It has been found that the peel resistance of the fastening device 52 increases when the bottom surface 82 is disposed around the entire stem 76 because more fiber elements 62 are engaged by each head 78. The bottom surface 82 may have any shape such as a planar or curvilinear surface. A curvilinear, convex bottom surface 82 is preferred to provide greater surface area for engaging the maximum number of fiber elements 62.

As shown in FIG. 4, the head 78 is also provided with a overhang, "Z", which defines the radial distance that the bottom surface 82 extends beyond the stem 76. The width of the overhang has been found especially important in providing a fastening device 52 having the desirable peel resistance. It has been found that as the width of the overhang increases, the peel resistance also increases. It is believed that the width of the overhang in comparison to the diameter of the fiber elements 62 determines how many fiber elements 62 or loops 64 may be engaged by each head 78. Thus, the ratio of the width of the overhang to the diameter of the fiber elements 62 is especially important in determining whether sufficient peel resistance exists in a fastening device 52. It has been found that the ratio of the width of the overhang to the diameter of the fiber elements 62, the fiber overhang ratio, should preferably be at least about 2:1 and more preferably at least about 3:1 to provide a fastening device 52 having the desired peel resistance. It should be understood that the ratios described in this application should be calculated using an average value for the dimensions of the elements of the first and second members 53 and 54 using a representative sample taken from each member.

The width of the overhang in comparison to the diameter of the stem 76 is also a consideration in determining the amount of peel resistance. The ratio of the width of the overhang to the diameter of the stem 76, the stem overhang ratio, should be at least about 0.1:1 and more preferably about 0.4:1.

The available height of the engaging element 74 in comparison to the diameter of the fiber elements 62 is also an important criteria for providing a fastening device 52 having the desired peel resistance. As shown in FIG. 4, the height of the engaging element 74 is defined as the perpendicular measurement from the lowest portion of the bottom surface 82 of the head 78 to the base 68, the distance designated by the letter "H". It is believed that as the height of the engaging element 74 increases in comparison to the diameter of the fiber elements 62, the peel resistance of the fastening device 52 also increases due to the fact that more fiber elements 62 will be able to move between the base 68 and the bottom surface 82 and engage the bottom surface 82. Thus, it has been found that the ratio of the height of the engaging elements 74 to the diameter of the fiber elements 62, the height ratio, should be at least about 5:1, and more preferably about 7:1.

The engaging elements 74 are preferably flexible and resilient to provide a fastening device 52 having increased peel resistance and increased skin friendliness. A suitable engaging elements 74 may be manufactured from a wide range of materials such as nylon, polypropylene, polyester or any combination thereof. A particularly preferred engaging element 74 is made of polypropylene. A number of manufacturing techniques may be used to manufacture the engaging elements 74. For example, the engaging elements 74 may be molded or heat formed. Preferred engaging elements 74 are heat formed by exposing the ends of the stem 76 to a heat source whereupon the head 78 is formed by the melting of the stem 76 to form a semi-spherical head 78. An example of such a heat forming process is disclosed in U.S. Pat. No. 3,138,841 issued to Naimer on June 30, 1964.

An exemplary embodiment of the engaging elements 74 of the present invention comprises a mushroom-like structure having a stem 76 having a height of approximately 0.47 millimeters and a diameter of 0.25 millimeters. The total height of each engaging element 74 is about 0.68 millimeters and the average height, "H", of the heads 78 above the base 68 is about 0.37 millimeters. The diameter of the head 78 measured across the base of the head is about 0.39 millimeters such that the head 78 has an overhang width along each radius of about 0.07 millimeters. Therefore, since the preferred fiber elements 62 of the first member 53 have a diameter of 0.027 millimeters, the fastening device 52 will have a fiber overhang ratio of about 2.6:1, a height ratio of about 13.7:1, and a stem overhang ratio of about 0.28:1.

Another example of the engaging elements 74 of the present invention comprises a structure in which the bottom surface extends radially outward from two radii. The stem 76 has a diameter of about 0.25 mm. The total height of each engaging element 74 is about 0.84 mm and the average height, "H", of the heads 78 above the base 68 is about 0.50 mm. The diameter of the head 78 measured across the base of the head is about 0.63 mm such that the head has an overhang width along each radius of about 0.19 mm. Therefore, since the preferred fiber elements 62 of the first member 53 have a diameter of 0.027 millimeters, the fastening device 52 will have a fiber overhang ratio of about 7:1, a height ratio of about 18:1, and a stem overhang ratio of about 0.73:1.

The second member 54 may comprise any of the well known configurations for achieving a side closure on a disposable diaper 10 such as a strip or patch of material. As shown in FIGS. 1 and 2, the second member 54 is preferably positioned on a fastening tape 55. Any of the well known configurations and constructions may be used as the fastening tape 55. A preferred fastening tape 55 is a Y-shaped tape as described in detail in U.S. Pat. No. 3,848,594 entitled "Tape Fastenings System For Disposable Diaper" which issued to K. B. Buell on Nov. 19, 1974, and which patent is incorporated herein by reference. Alternatively preferred fastening tapes are described in detail in abandoned U.S. patent application Ser. No. 821,100 entitled "Disposable Diaper Having Wide Tapered Fastening Tapes" filed Jan. 21, 1986 by H. R. Burkhard and K. B. Buell; and U.S. patent application Ser. No. 842,326, U.S. Pat. No. 4,699,622, entitled "Disposable Diaper Having An Improved Side Closure" filed Mar. 21, 1986 by J. W. Toussant and M. H. Hasse, both of which are incorporated herein by reference. As shown in FIG. 1, a fastening tape 55 is provided on both the first and second longitudinal sides, 26 and 28, respectively, of the diaper 10.

The preferred fastening tape 55 illustrated in FIG. 2 has a manufacturer's end 56 and a user's end 58 having a fastening surface 60. The manufacturer's end 56 is that end of the fastening tape 55 which the manufacturer of the diaper 10 affixes to the diaper 10 while the user's end 58 is that end of the fastening tape 55 which the user affixes to the first member 53 when fitting the diaper 10 to the wearer. The manufacturer's end 56 is affixed to the first waist portion 42, and after fitting the diaper 10 about the waist of the wearer, the fastening surface 60 of the user's end 58 is affixed to the first member 53 preferably positioned on the second waist portion 44 thereby causing the diaper 10 to encirle the waist of the wearer and effecting a side closure. The engaging elements 74 extend from the fastening surface 60 of the user's end 58 so that the engaging elements 74 contact the fiber elements 62 of the first member 53. A preferred configuration for the fastening surface 60 of the fastening tape 55 that minimizes any possible contact between the fastening device 52 and the skin of the wearer is described in the above-referenced U.S. patent application Ser. No. 821,100 by Burkhard and Buell.

In use, the diaper 10 is applied to the wearer by positioning the first waist portion 42 under the wearer's back and drawing the remainder of the diaper 10 between the legs of the wearer so that the second waist portion 44 is positioned across the front of the wearer. The user's end 58 of the fastening tape 55 are then secured to the first member 53 on the outside surface of the second waist portion 44 so that the second member 54 which is disposed on the fastening surface 60 of the fastening tapes 55 will engage the first member 53 to form a side closure.

The shear stress resistance of the fastening device 52 is a measure of the ability of the fastening device 52 to resist the forces that induce shear stress and thus prevent the first member 53 and the second member 54 from disengaging during use. The shear resistance of the fastening device 52 may be determined using any method which measures the force required to first initiate movement between the first and second member 53 and 54 at a contact pressure of 17 grams/square centimeter. A suitable procedure is described in more detail in the above referenced U.S. patent application Ser. No. 842,326 of Toussant and Hasse.

The peel resistance of the fastening device 52 is a measure of the ability of the fastening device 52 to resist peel forces and thus prevent the first and second waist portions 42 and 44 from separating or from allowing the first member 53 to separate from the second member 54 when they are in contact. The peel resistance of the fastening device 52 may be determined using any method which measures the force required to peel the second member 54 from the first member 53 at a contact pressure of about 4.5 pounds. The following procedure for determining the peel resistance of the fastening device 52 was used with good results. A first sample is prepared from the first member 53 and a second sample is prepared from the second member 54. Each of the samples should be one inch in the cross machine direction and long enough in the machine direction to perform the required test.

The first sample is affixed to a 135° test jig with the fiber elements 62 facing away from the panel. The second sample is placed onto the first sample prepared in the preceding step. The second sample is centered on the first sample with the long dimension of the second sample parallel to the long dimension of the first sample. The second sample is immediately rolled down its length with one pass in each direction of a 4.5 pound mechanically operated roller to simulate the condition when the diaper 10 is worn. A peel force is then applied to the engaged samples along a 135° angle and an average of the four highest peak force values is used to determine the force required to peel the first sample from the second sample, the peel resistance of the fastening device 52. The peel force may be applied and measured using any technique or apparatus that will be known to those skilled in the testing art. It has been found, however, that the peel resistance of the fastening device 52 may easily be determined using a tensile tester of the types manufactured by Instron Corporation of Canton, Mass. and marketed under the tradename Instron 1101-TM 1102-TMS 1122 and 1130.

While particular embodiments of the present invention have been described, it would be obvious to those skilled in the art that various other changes and modifications can be made without departing from the spirit and scope of the invention. It is therefore intended to cover in the appended claims all such changes and modifications that are within the scope of the invention.

What is claimed is:

1. A disposable diaper comprising:
   a liquid pervious topsheet;
   a liquid impervious backsheet, said backsheet being affixed to said topsheet;
   an absorbent core for absorbing liquids, said absorbent core being encased between said topsheet and said backsheet;
   a longitudinal marginal portion adjacent each longitudinal side of the disposable diaper;
   an elastic member operatively associated with each of said longitudinal marginal portions;
   a first waist portion at one end of the disposable diaper;
   a second waist portion at the opposite end of the disposable diaper; and a fastening device for maintaining said first waist portion and said second waist portion in an overlapping configuration during use, said fastening device comprising:
   a first member comprising a plurality of fiber elements; and
   a second member engagable with said fiber elements of said first member, said second member comprising:
      (a) a base having a first surface and a second surface, and
      (b) a plurality of engaging elements extending from said first surface of said base, each of said engaging elements comprising:
         (i) a stem supported at one end thereof on said base, and
         (ii) an enlarged head positioned at the end of said stem opposite said base, said head having a smooth, generally convex top surface and a bottom surface extending radially outwardly from said stem along at least two radii of said stem to the periphery of said top surface, said bottom surface adapted to be engaged by at least one of said fiber elements, wherein the ratio of the width of the overhang of said engaging elements to the diameter of said fiber elements, the fiber overhang ratio, is at least about 2:1 and the ratio of the height of said engaging elements to the diameter of said fiber elements, the height ratio, is at least about 5:1.

2. The disposable diaper of claim 1 wherein said bottom surface of said head extends radially outwardly along each radius of said stem.

3. The disposable diaper of claim 2 where said bottom surface is planar.

4. The disposable diaper of claim 2 wherein said bottom surface is curvilinear.

5. The disposable diaper of claim 1 wherein said top surface of said head is semi-spherical.

6. The disposable diaper of claim 1 wherein said engaging elements comprise a polypropylene.

7. The disposable diaper of claim 1 wherein said fastening device has a ratio of the width of the overhang of said engaging elements to the diameter of said stem, the stem overhang ratio, of at least about 0.1:1.

8. The disposable diaper of claim 1 wherein said engaging elements are disposed relative to said base at an angle of between about 30° and about 90°.

9. The disposable diaper of claim 8 wherein said engaging elements are disposed relative to said base at an angle of between about 45° and about 75°.

10. The disposable diaper of claim 1 wherein said engaging elements are disposed on said base at a density of at least about 100 engaging elements per square inch.

11. The disposable diaper of claim 1 wherein said fastening device additionally comprises a fastening tape secured on each longitudinal side of the diaper on said first waist portion, each of said fastening tapes having a manufacturer's end and a user's end, and wherein said second member is positioned on said user's end of each said fastening tapes.

12. The disposable diaper of claim 1 wherein said first member is secured to the outside of said second waist portion and said second member is secured to the inside of each side of said first waist portion.

13. A disposable diaper comprising:
   a liquid pervious topsheet;
   a liquid impervious backsheet, said backsheet being affixed to said topsheet;
   an absorbent core for absorbing liquids, said absorbent core being encased between said topsheet and said backsheet;
   a longitudinal marginal portion adjacent each longitudinal side of the disposable diaper;
   an elastic member operatively associated with each of said longitudinal marginal portions;
   a first waist portion at one end of the disposable diaper;
   a second waist portion at the opposite end of the disposable diaper; and
   a fastening device for maintaining said first waist portion and said second waist portion in an overlapping configuration during use, said fastening device comprising:
      a first member comprising a plurality of fiber elements, said first member positioned on the outside of said second waist portion;
      a fastening tape affixed to each longitudinal edge of said first waist portion, said fastening tape having a manufacturer's end and a user's end; and
      a second member engagable with said fiber elements of said first member, and positioned on said user's end of said fastening tape, said second member comprising:
         (a) a flexible base having a first surface and a second surface, and
         (b) a plurality of engaging elements extending from said first surface of said base at an angle between about 30° and about 90°, each of said engaging elements comprising:
            (i) a stem supported on one end thereof on said base, and
            (ii) an enlarged head positioned at the end of said stem opposite said base, said head having a smooth generally semi-spherical top surface and a bottom surface extending radially outwardly of each radius from said stem to the periphery of said top surface, said bottom surface adapted to be engaged by at least one of said fiber elements, wherein the ratio of the width of the overhang of said engaging elements to the diameter of said fiber elements, the fiber overhang ratio, is at least about 2:1 and the ratio of the height of said engaging elements to the diameter of said fiber elements, the height ratio, is at least 5:1.

14. The disposable diaper of claim 13 wherein said fiber overhang ratio is at least about 3:1.

15. The disposable diaper of claim 14 wherein said height ratio is at least about 7:1.

16. The disposable diaper of claim 15 wherein said fastening device has a ratio of the width of the overhang of said engaging elements to the diameter of said stem, the stem overhang ratio, of at least about 0.1:1.

17. The disposable diaper of claim 16 wherein said engaging elements are disposed relative to said base at an angle of between about 45° and about 75°.

18. The disposable diaper of claim 17 wherein said engaging elements are polypropylene.

19. The disposable diaper of claim 18 wherein said fastening device has a resistance to peel forces of at least about 200 grams.

20. The disposable diaper of claim 19 wherein said engaging elements are disposed on said base at a density of at least about 100 engaging elements per square inch.

* * * * *

UNITED STATES PATENT AND TRADEMARK OFFICE
CERTIFICATE OF CORRECTION

PATENT NO. : 4,846,815

DATED : July 11, 1989

INVENTOR(S) : CHARLES L. SCRIPPS

It is certified that error appears in the above-identified patent and that said Letters Patent is hereby corrected as shown below:

Column 2, Line 13,     "suffient" should read ---sufficient---.

Column 2, Line 20,     "Thus, it would advantageous" should read ---Thus, it would be advantageous---.

Column 7, Line 21,     "As used herein" should read ---As used herein,---.

Column 8, Lines 24-25     "As used herein" should read ---As used herein,---.

Column 8, Lines 57-58,     "In addition it" should read ---In addition, it---.

Column 13, Line 41,     "encirle" should read ---encircle---.

Signed and Sealed this

Fifteenth Day of May, 1990

Attest:

HARRY F. MANBECK, JR.

*Attesting Officer*     *Commissioner of Patents and Trademarks*